United States Patent
Hwang et al.

(10) Patent No.: US 11,540,737 B2
(45) Date of Patent: Jan. 3, 2023

(54) APPARATUS AND METHOD FOR MEASURING BIO-INFORMATION

(71) Applicant: SAMSUNG ELECTRONICS CO., LTD., Suwon-si (KR)

(72) Inventors: Jeong Eun Hwang, Suwon-si (KR); Byung Hoon Ko, Hwaseong-si (KR); Jong Wook Lee, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 133 days.

(21) Appl. No.: 16/822,901

(22) Filed: Mar. 18, 2020

(65) Prior Publication Data

US 2021/0038098 A1 Feb. 11, 2021

(30) Foreign Application Priority Data

Aug. 5, 2019 (KR) .................. 10-2019-0094821

(51) Int. Cl.
*A61B 5/024* (2006.01)
*A61B 5/022* (2006.01)
(Continued)

(52) U.S. Cl.
CPC ...... *A61B 5/02438* (2013.01); *A61B 5/02225* (2013.01); *A61B 5/02416* (2013.01);
(Continued)

(58) Field of Classification Search
CPC ............ A61B 5/02438; A61B 5/02225; A61B 5/02416; A61B 5/681; A61B 5/684;
(Continued)

(56) References Cited

U.S. PATENT DOCUMENTS 6,120,459 A * 9/2000 Nitzan ................. A61B 5/6838
600/490
9,592,007 B2 3/2017 Nuovo et al.
(Continued)

FOREIGN PATENT DOCUMENTS

KR 10-0640838 B1 11/2006
KR 10-1075507 B1 10/2011
(Continued)

OTHER PUBLICATIONS

Communication dated Oct. 30, 2020, from the European Patent Office in counterpart European Application No. 20173613.9.

*Primary Examiner* — Devin B Henson
*Assistant Examiner* — Justin Xu
(74) *Attorney, Agent, or Firm* — Sughrue Mion, PLLC

(57) ABSTRACT

An apparatus for measuring bio-information may include a pulse wave sensor that may measure a pulse wave signal from an object in contact with a measurement surface. The apparatus may include a force sensor that may measure a contact force between the pulse wave sensor and the object. The apparatus may include a fastener configured to fasten the pulse wave sensor to an electronic device such that the pulse wave sensor is rotatable around a center axis in a length direction of the pulse wave sensor. The apparatus may include a processor that may determine a direction in which a measurement region of the pulse wave signal or the measurement surface of the pulse wave sensor is oriented, select a measurement mode from among a plurality of measurement modes, and estimate bio-information of the object.

19 Claims, 24 Drawing Sheets

(51) Int. Cl.
*A61B 5/00* (2006.01)
*A61B 5/0225* (2006.01)
*A61B 5/021* (2006.01)
*A61B 5/02* (2006.01)

(52) U.S. Cl.
CPC .............. *A61B 5/681* (2013.01); *A61B 5/684* (2013.01); *A61B 5/6843* (2013.01)

(58) Field of Classification Search
CPC .......... A61B 5/6843; A61B 2562/0238; A61B 5/02255; A61B 5/02427; A61B 5/02108; A61B 5/02007; A61B 5/6802; A61B 5/6803; A61B 5/7235; A61B 5/7275
See application file for complete search history.

(56) References Cited

U.S. PATENT DOCUMENTS

| | | | |
|---|---|---|---|
| 10,238,312 B2 | 3/2019 | Eom et al. | |
| 10,285,599 B2 | 5/2019 | Fortin | |
| 10,390,710 B2* | 8/2019 | Umeda | A61B 5/02233 |
| 10,694,958 B2 | 6/2020 | Fortin | |
| 10,835,132 B2* | 11/2020 | Qasem | A61B 5/02108 |
| 10,973,422 B2* | 4/2021 | Pantelopoulos | A61B 5/7285 |
| 2012/0259190 A1* | 10/2012 | Baker, Jr. | A61B 5/02416 600/324 |
| 2013/0289366 A1* | 10/2013 | Chua | A61B 5/14552 600/324 |
| 2016/0089053 A1 | 3/2016 | Lee et al. | |
| 2016/0198955 A1* | 7/2016 | Fortin | A61B 5/721 600/323 |
| 2016/0235364 A1* | 8/2016 | Yoshida | A61B 5/681 |
| 2016/0278645 A1 | 9/2016 | Yoon | |
| 2017/0042433 A1* | 2/2017 | Noh | A61B 5/1118 |
| 2017/0209055 A1 | 7/2017 | Pantelopoulos et al. | |
| 2018/0042554 A1 | 2/2018 | Wagner et al. | |
| 2018/0184919 A1 | 7/2018 | Nakazawa et al. | |
| 2018/0212449 A1 | 7/2018 | Park et al. | |
| 2019/0038154 A1* | 2/2019 | Fujita | A61B 5/02108 |
| 2019/0044694 A1 | 2/2019 | Raj et al. | |
| 2019/0298193 A1* | 10/2019 | Krause | A61B 5/02116 |

FOREIGN PATENT DOCUMENTS

| | | |
|---|---|---|
| KR | 10-1448135 B1 | 10/2014 |
| KR | 10-1528246 B1 | 6/2015 |
| KR | 10-1798495 B1 | 11/2017 |
| KR | 10-1907675 B1 | 10/2018 |
| KR | 10-2020-0110116 A | 9/2020 |
| WO | 2016110781 A1 | 7/2016 |

* cited by examiner

APPARATUS AND METHOD FOR MEASURING BIO-INFORMATION

CROSS-REFERENCE TO RELATED APPLICATION(S)

This application is based on and claims priority under 35 U.S.C. § 119 to Korean Patent Application No. 10-2019-0094821, filed on Aug. 5, 2019, in the Korean Intellectual Property Office, the disclosure of which is incorporated by reference herein in its entirety.

BACKGROUND

1. Field

The disclosure relates to an apparatus and method for measuring bio-information.

2. Description of Related Art

Healthcare technology has attracted much attention due to the rapid entry into an aging society and relevant social problems such as an increase in medical expenses. Accordingly, medical devices that can be utilized by hospitals and inspection agencies, and also small-sized medical devices that can be carried by individuals such as wearable devices are being developed. In addition, such a small-sized medical device is worn by a user in the form of a wearable device capable of directly measuring cardiovascular health status such as blood pressure, or the like, so that the user can directly measure and manage cardiovascular health status.

Therefore, research on a method of estimating a blood pressure by analyzing bio-information is being actively conducted for miniaturization of a device.

SUMMARY

Additional aspects will be set forth in part in the description which follows and, in part, will be apparent from the description, or may be learned by practice of the presented embodiments.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The disclosure relates to an apparatus and method for estimating bio-information using different algorithms based on a direction in which a measurement region of a pulse wave signal or a measurement surface of a pulse wave sensor is oriented.

According to an aspect of the disclosure, an apparatus for measuring bio-information may include a pulse wave sensor that may measure a pulse wave signal from an object in contact with a measurement surface. The apparatus may include a force sensor that may measure a contact force between the pulse wave sensor and the object. The apparatus may include a fastener configured to fasten the pulse wave sensor to an electronic device such that the pulse wave sensor is rotatable around a center axis in a length direction of the pulse wave sensor. The apparatus may include a processor that may determine a direction in which a measurement region of the pulse wave signal or the measurement surface of the pulse wave sensor is oriented, select a measurement mode from among a plurality of measurement modes based on the direction in which the measurement region of the pulse wave signal or the measurement surface of the pulse wave sensor is oriented, and estimate bio-information of the object based on the measured pulse wave signal and the measured contact force in the selected measurement mode.

The measurement surface of the pulse wave sensor may be formed as a curved surface protruding toward a contact surface of the object.

The processor may determine the measurement region of the pulse wave signal based on a waveform of the measured pulse wave signal.

The processor may compare the measured pulse wave signal to a first reference waveform and a second reference waveform, select a first measurement mode based on determining that a waveform of the measured pulse wave signal is similar to the first reference waveform, and select a second measurement mode based on determining that the waveform of the measured pulse wave signal is similar to the second reference waveform.

The first measurement mode may be a bio-information estimation mode using oscillometry, and the second measurement mode may be a bio-information estimation mode using pulse waveform analysis.

The pulse wave sensor may have a center of gravity biased toward one side in a height direction, and the processor may determine the direction in which the measurement surface of the pulse wave sensor is oriented based on a position of the center of gravity.

The processor may select a first measurement mode based on determining that the measurement surface of the pulse wave sensor is oriented in a first direction, and select a second measurement mode based on determining that the measurement surface of the pulse wave sensor is oriented in a second direction.

Based on a first measurement mode being selected from among the plurality of measurement modes, the processor may acquire an oscillometric signal using the measured pulse wave signal and the measured contact force and estimate the bio-information by analyzing the acquired oscillometric signal.

Based on a first measurement mode being selected from among the plurality of measurement modes, the processor may generate contact force guide information for informing a user of an amount of contact force to be added or reduced to the pulse wave sensor based on the measured contact force.

Based on a second measurement mode being selected from among the plurality of measurement modes, the processor may determine whether a contact between the pulse wave sensor and the object is adequate based on the measured contact force and estimate the bio-information by analyzing a waveform of the measured pulse wave signal based on determining that the contact is adequate.

Based on determining that the contact is not adequate, the processor may generate and provide action guide information for inducing adequate contact.

Based on determining that the contact is adequate, the processor may extract one or more features from the measured pulse wave signal and estimate the bio-information using the one or more extracted features and a bio-information value estimated in a first measurement mode among the plurality of measurement modes.

The apparatus may include an anti-slip portion configured to prevent the object in contact with the measurement surface of the pulse wave sensor from slipping away from the measurement surface.

The anti-slip portion may be formed on an edge of the pulse wave sensor in a direction parallel to a length direction of the pulse wave sensor.

The pulse wave sensor may rotate around the center axis in the length direction in a state of being fastened to the electronic device, and the fastener may include a braking portion that may stop rotation of the pulse wave sensor based on the measurement surface of the pulse wave sensor being oriented in a first direction or a second direction.

The electronic device may be a wrist wearable device, and the apparatus may be applied to one of a strap connector of a main body of the wrist wearable device, a button or an edge of the main body of the wrist wearable device, and a strip of the wrist wearable device.

According to an aspect of the disclosure, a method of measuring bio-information which is performed by an apparatus for measuring bio-information which may include a pulse wave sensor and is fastened to an electronic device so as to be rotatable around a center axis of a length direction, may include determining a direction in which a measurement region of a pulse wave signal or a measurement surface of the pulse wave sensor is oriented; selecting a measurement mode from among a plurality of measurement modes based on the direction in which the measurement region of the pulse wave signal or the measurement surface of the pulse wave sensor is oriented; measuring the pulse wave signal from an object in contact with the measurement surface of the pulse wave sensor; measuring a contact force between the pulse wave sensor and the object; and estimating bio-information based on the measured pulse wave signal and the measured contact force in the selected measurement mode.

The determining of the direction in which the measurement region of the pulse wave signal or the measurement surface of the pulse wave sensor is oriented may include measuring the pulse wave signal from the object in contact with the measurement surface of the pulse wave sensor, and determining the measurement region of the pulse wave signal based on a waveform of the measured pulse wave signal.

The determining of the measurement region of the pulse wave signal may include comparing the measured pulse wave signal to a first reference waveform and a second reference waveform; determining that the measurement region of the pulse wave signal is a first region based on determining that a waveform of the measured pulse wave signal is similar to the first reference waveform; and determining that the measurement region of the pulse wave signal is a second region based on determining that the waveform of the measured pulse wave signal is similar to the second reference waveform. The selecting of the measurement mode from among the plurality of measurement mode may include selecting a first measurement mode based on determining that the measurement region is the first region and selecting a second measurement mode based on determining that the measurement region is the second region.

The first measurement mode may be a bio-information estimation mode using oscillometry, and the second measurement mode may be a bio-information estimation mode using pulse waveform analysis.

The pulse wave sensor may have a center of gravity biased toward one side in a height direction. The determining of the direction in which the measurement region of the pulse wave signal or the measurement surface of the pulse wave sensor is oriented may include determining the direction in which the measurement surface of the pulse wave sensor is oriented based on a position of the center of gravity.

The selecting of measurement mode from among the plurality of measurement modes may include selecting a first measurement mode based on determining that the measurement surface of the pulse wave sensor is oriented in a first direction, and selecting a second measurement mode based on determining that the measurement surface of the pulse wave sensor is oriented in a second direction.

The estimating of the bio-information may include, based on a first measurement mode being selected from among the plurality of measurement modes, acquiring an oscillometric signal using the measured pulse wave signal and the measured contact force; and estimating the bio-information based on the acquired oscillometric signal.

The method may include, based on a first measurement mode being selected from among the plurality of measurement modes, generating and providing contact force guide information for informing a user of an amount of contact force to be added or reduced to the pulse wave sensor based on the measured contact force.

The measuring of the bio-information may include, based on a second measurement mode being selected from among the plurality of measurement modes, determining whether a contact between the pulse wave sensor and the object is adequate based on the measured contact force; and estimating the bio-information based on a waveform of the measured pulse wave signal based on determining that the contact is adequate.

The estimating of the bio-information may include, based on determining that the contact is not adequate, generating and providing action guide information for inducing adequate contact.

The estimating of the bio-information may include, based on determining that that the contact is adequate, extracting one or more features from the measured pulse wave signal; and estimating the bio-information using the one or more extracted features and a bio-information value estimated in a first measurement mode among the plurality of measurement modes.

The electronic device may be a wrist wearable device and the apparatus may be applied to one of a strap connector of a main body of the wrist wearable device, a button or an edge of the main body of the wrist wearable device, and a strip of the wrist wearable device.

Other features and aspects will be apparent from the following detailed description, the drawings, and the claims.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
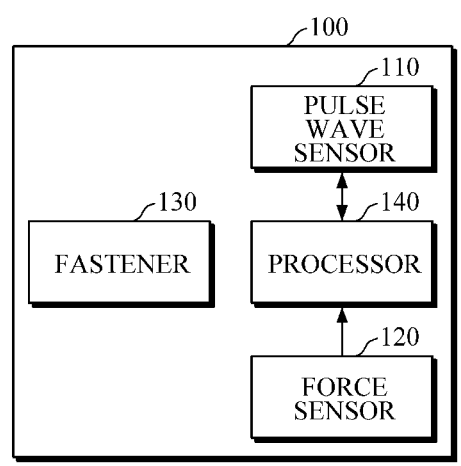
FIG. 1 is a diagram illustrating an apparatus for measuring bio-information according to an embodiment.

Throughout the drawings and the detailed description, unless otherwise described, the same drawing reference numerals may refer to the same elements, features, and structures. The relative size and depiction of these elements, features, and structures may be exaggerated for clarity, illustration, and convenience.

DETAILED DESCRIPTION

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It should be noted that in some alternative implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved.

Terms described herein are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

As used herein, the singular forms of terms may include the plural forms of the terms as well, unless the context clearly indicates otherwise. It will be further understood that terms such as "comprises," "comprising," "includes," "including," and the like, when used in this description, specify the presence of stated features, numbers, steps, operations, elements, components or combinations thereof, but do not preclude the presence or addition of one or more other features, numbers, steps, operations, elements, components or combinations thereof.

It will also be understood that the elements or components in the following description are discriminated in accordance with their respective main functions. In other words, two or more elements may be integrated into a single element or a single element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

Figure 2:
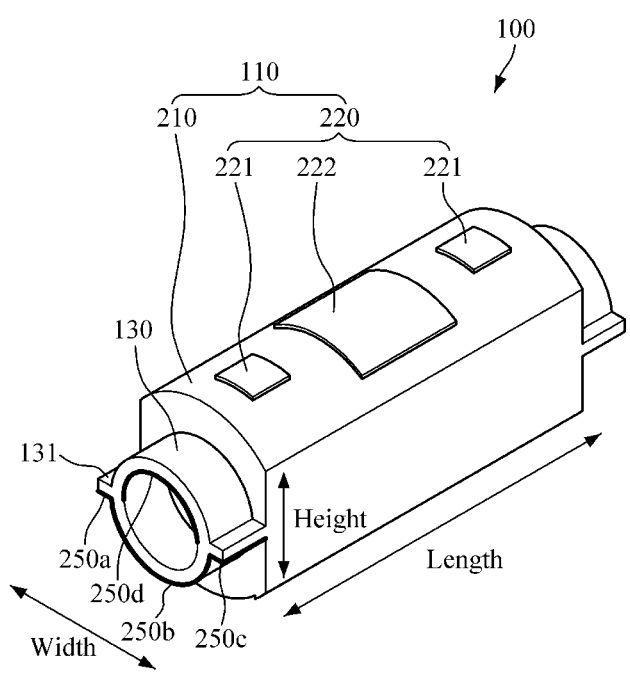
FIG. 2 is a perspective view of the apparatus for measuring bio-information according to an embodiment.

FIG. 1 is a diagram illustrating an apparatus for measuring bio-information according to an embodiment, and FIG. 2 is a perspective view of the apparatus for measuring bio-information according to an embodiment.

The apparatus 100 for measuring bio-information shown in FIG. 1 may be an apparatus that is rotatably mounted in an electronic device, and configured to measure bio-information by selecting a different measurement mode based on a measurement region of a pulse wave signal. In this case, the electronic device may include a mobile phone, a smartphone, a tablet device, a notebook computer, a personal digital assistant (PDA), a portable multimedia player (PMP), a navigation device, an MP3 player, a digital camera, a wearable device, and the like. The wearable device may include a wrist watch type, a wrist band type, a ring type, a belt type, a necklace type, an ankle band type, a thigh band type, a forearm band type, and the like. However, the electronic device and the wearable device are not limited to the above-described examples. The bio-information may include, but is not limited to, blood pressure, vascular age, a degree of arteriosclerosis, a stress index, a degree of fatigue, and the like. Hereinafter, for convenience of description, blood pressure will be taken as an example and described.

Referring to FIGS. 1 and 2, the apparatus 100 for measuring bio-information may include a pulse wave sensor 110, a force sensor 120, a fastener 130, and a processor 140.

The pulse wave sensor 110 may measure one or a plurality of pulse wave signals from an object in contact with a measurement surface. Here, the pulse wave signal may be a photoplethysmogram (PPG) signal. When the pulse wave sensor 110 measures a plurality of pulse wave signals, the pulse wave sensor 110 may measure the pulse wave signals using light of different wavelengths. Here, the object may be a peripheral part of a body, such as a finger, a toe, or the like, or a region of a wrist surface near the radial artery.

The pulse wave sensor 110 may include a housing 210 and a pulse wave measurer 220.

The housing 210 may be formed such that the measurement surface to be in contact with the object is a curved surface protruding to a contact surface of the object. According to an embodiment, when a finger comes in contact with the measurement surface of the housing 210, the housing 210 may be formed to be smaller than the size of the finger such that the contact area can be constant. For example, the housing 210 may be formed to be smaller than an average size of fingers of a plurality of users by taking into account the user's age and sex, and the type of a finger to use (e.g., a thumb, an index finger, a middle finger, a ring finger, and a little finger).

The elasticity of the finger may be affected by a structure of the object in contact with the finger. For example, when comparing the case of a curved object in contact and the case of a flat object in contact, the curved object may cause a deeper layer of the skin to deform than the flat object when the same force is applied. Thus, the pulse wave sensor 110 according to an embodiment may be formed to have the curved measurement surface, which is to be in contact with the finger, so that, with less force, the same pressure as that exerted when the measurement surface is flat may be applied to the finger. Through this structure of the housing 210, a pressure may be delivered to the inside of the finger with less force as compared to the flat structure, and thus it is possible to reach a maximum pulse pressure when a blood pressure is measured using oscillometry. In addition, with the above-described housing structure, which allows the pulse wave sensor to be positioned accurately and close to a target (e.g., blood vessel, and the like) from which bio-information is to be acquired, the apparatus 100 for measuring bio-information may acquire information on the inside of the finger (e.g., blood vessels and blood inside the skin and the like).

The pulse wave measurer 220 may be mounted in the housing 210 and measure one or a plurality of pulse wave signals from the object in contact with the measurement surface of the housing 210. According to an embodiment, the pulse wave measurer 220 may include two light sources 221 configured to emit light of a predetermined wavelength to the object in contact with the measurement surface, and a photodetector 222 configured to receive light returning from the object. However, this is merely illustrative for convenience of description, and the number of the light sources 221 and the number of photodetectors 222 are not particularly limited.

According to an embodiment, as shown in FIG. 2, the photodetector 222 may be disposed at the center of the curved surface, which is the measurement surface, and the two light sources 221 may be disposed symmetrically around the photodetector 222 in a length direction of the pulse wave sensor 110 or in a tangential direction of the curved surface. In this case, the two light sources 221 may be disposed inward (e.g., 0.1 L to 0.9 L (here, "L" is a length of the pulse wave sensor)) of an edge portion to reduce the effect of the pressure or force.

According to an embodiment, the light source 221 may include a light emitting diode (LED), a laser diode, and a phosphor, but is not limited thereto. In addition, the photodetector 222 may include a photodiode, a photo transistor, an image sensor (e.g., a charge-coupled device (CCD), a complementary metal-oxide semiconductor (CMOS), or the like, but is not limited thereto.

The force sensor 120 may measure a contact force between the object and the pulse wave sensor 110. The force sensor 120 may be disposed at an inner surface 250d of the fastener in the same direction as the measurement surface of the pulse wave sensor 110 or outer surfaces 250a, 250b, and 250c of the fastener in a direction opposite to the measurement surface of the pulse wave sensor 110. According to an embodiment, the force sensor 120 may measure a force applied to the force sensor 120 in accordance with the contact between the object and the pulse wave sensor 110 as the contact force between the object and the pulse wave sensor 110. The force sensor 120 may include a voltage resistive force sensor, an ultrasonic force sensor, a load cell sensor, a pyroelectric force sensor, a strain gauge force sensor, an electrochemical force sensor, an optical force sensor, a magnetic force sensor, and the like.

The fastener 130 may be fastened to the electronic device such that the pulse wave sensor 110 is rotatable around a center axis in the length direction of the pulse wave sensor 110. According to an embodiment, where the pulse wave sensor 110 rotates around the center axis in the length direction of the pulse wave sensor 110 in a state of being fastened to the electronic device, the fastener 130 may include a braking portion 131 that stops rotation of the pulse wave sensor 110 when the measurement surface of the pulse wave sensor 110 is oriented in a first direction or a second direction. In the case where the pulse wave sensor 110 rotates in a state of being fastened to the electronic device, it is possible to stop the rotation of the pulse wave sensor 110 through the braking portion 131 when the measurement surface of the pulse wave sensor 110 is positioned in a desired direction.

The processor 140 may control the overall operation of the apparatus 100 for measuring bio-information.

The processor 140 may control the pulse wave sensor 110 to measure one or a plurality of pulse wave signals for bio-information measurement. The processor 140 may generate a pulse wave sensor control signal to control the pulse wave sensor 110 based on a request for bio-information measurement being received from a user based on a user input. A sensor driving condition for controlling the pulse wave sensor 110 may be stored in a storage device in advance. The processor 140 may control the pulse wave sensor 110 based on the sensor driving condition stored in the storage device based on the request for bio-information measurement being received. In this case, the sensor driving condition may include emission time of each light source, driving order of the light sources, current intensity, pulse duration, and the like.

The processor 140 may determine a direction in which the measurement region of the pulse wave signal or the measurement surface of the pulse wave sensor 110 is oriented.

According to an embodiment, the processor 140 may determine the measurement region of the pulse wave signal based on a waveform of the pulse wave signal measured through the pulse wave sensor 110. For example, the processor 140 may compare the waveform of the measured pulse wave signal to a first reference waveform and a second reference waveform. Also, the processor 140 may determine that the measurement region of the pulse wave signal is a first region based on the waveform of the measured pulse wave signal being similar to the first reference waveform, and may determine that the measurement region of the pulse wave signal is a second region based on the waveform of the measured pulse wave signal being similar to the second reference waveform. The similarity may be determined based on whether the degree of similarity exceeds a predetermined reference value. The first region may be a finger and the second region may be a wrist. In addition, the first reference waveform may be a waveform of a pulse wave signal measured in advance from a finger, and the second reference waveform may be a waveform of a pulse wave signal measured in advance from a wrist.

Figure 3:
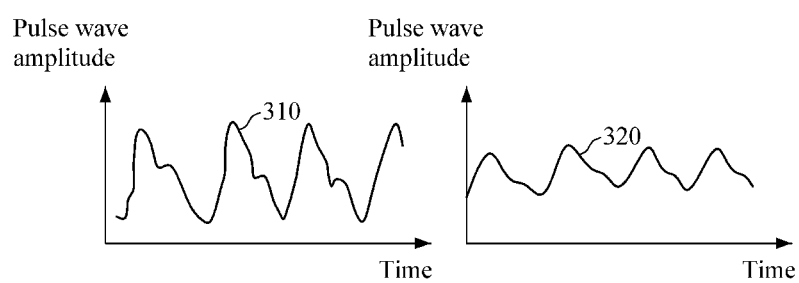
FIG. 3 illustrates graphs showing examples of pulse wave signals measured from a finger and a wrist according to an embodiment.

FIG. 3 illustrates graphs showing examples of pulse wave signals measured from a finger and a wrist. As shown in FIG. 3, a waveform of a pulse wave signal may differ depending on a measurement region of the pulse wave signal. In FIG. 3, a pulse wave signal 310 may be a pulse wave signal measured from a finger, and a pulse wave signal 320 may be a pulse wave signal measured from a wrist. As shown in FIG. 3, the pulse wave signal 310 measured from a finger may have a greater amplitude than that of the pulse wave signal 320 measured from a wrist, and may exhibit a more sharp waveform. Thus, the processor 140 may determine the measurement region of the measured pulse wave signal based on the waveform of the measured pulse wave signal.

According to another embodiment, the processor 140 may determine a direction in which the measurement surface of the pulse wave sensor 110 is oriented based on the position of the center of gravity of the pulse wave sensor 110 which has been detected by an orientation sensor. To this end, the pulse wave sensor 110 may have the center of gravity biased toward one side in a height direction thereof. That is, the processor 140 may determine whether the measurement surface of the pulse wave sensor 110 is oriented in a first direction or a second direction based on a position of the center of gravity of the pulse wave sensor 110. Here, the first direction is a direction in which the pulse wave signal of a finger can be measured, and the second direction is a direction in which the pulse wave signal of a wrist can be measured.

According to another embodiment, an apparatus 100 for measuring bio-information may further include an illuminance sensor, and the like. Based on an illuminance measured by the illuminance sensor, to the processor 140 may determine a direction in which the measurement surface of the pulse wave sensor 110 is oriented.

The processor 140 may select one of a first measurement mode and a second measurement mode based on the measurement region of the pulse wave signal or the direction in which the measurement surface of the pulse wave sensor 110 is oriented. In this case, the first measurement mode may be a blood pressure measurement mode using oscillometry, and the second measurement mode may be a blood pressure measurement mode using pulse wave analysis (PWA).

According to an embodiment, the processor 140 may select the first measurement mode based on determining that the measurement region of the pulse wave signal is a first region, for example, a finger, and may select the second measurement mode based on determining that the measurement region of the pulse wave signal is a second region, for example, a wrist.

According to another embodiment, the processor 140 may select the first measurement mode based on determining that the measurement surface of the pulse wave sensor 110 is oriented in the first direction, and may select the second measurement mode based on determining that the measurement surface of the pulse wave sensor 110 is oriented in the second direction.

Hereinafter, the first measurement mode and the second measurement mode will be separately described.

<First Measurement Mode>

In the first measurement mode, the processor 140 may operate as follows.

The processor 140 may generate contact force guide information for informing a user of an amount of contact force that the user should add or reduce on the pulse wave sensor 110 while measuring the pulse wave signal, and provide the contact force guide information to the user. The processor 140 may provide the contact force guide information to the user through an output component or interface, or may transmit the contact force guide information to an external device, for example, an electronic device, in which an apparatus for measuring bio-information is mounted, through a communication interface and provide the contact force guide information to the user through the electronic device.

The contact force guide information may be provided before, after, or at the same time as the start of the pulse wave signal measurement. The contact force information may be continuously provided while the pulse wave sensor 110 is measuring the pulse wave signal from a finger. The contact force guide information may be pre-set for each user based on user characteristics, such as the user's age, sex, and health status, a contact region of an object, and the like. The contact force guide information may be a contact force value itself that the user should add to or subtract from the pulse wave sensor 110, but is not limited thereto such that the contact force guide information may include motion information of the user for inducing a change in force applied by a finger to the pulse wave sensor 110.

The processor 140 may continuously receive a contact force value from the force sensor 120, and generate the contact force guide information based on the received contact force value and provide the contact force guide information to the user. For example, the processor 140 may provide the contact pressure guide information based on a difference between a contact force value at a specific point in time and a contact force value to be applied by the user to the pulse wave sensor 110 at the specific point in time.

The processor 140 may acquire an oscillometric signal using one or a plurality of pulse wave signals acquired through the pulse wave sensor 110 and the contact force acquired through the force sensor 120.

Figure 4:
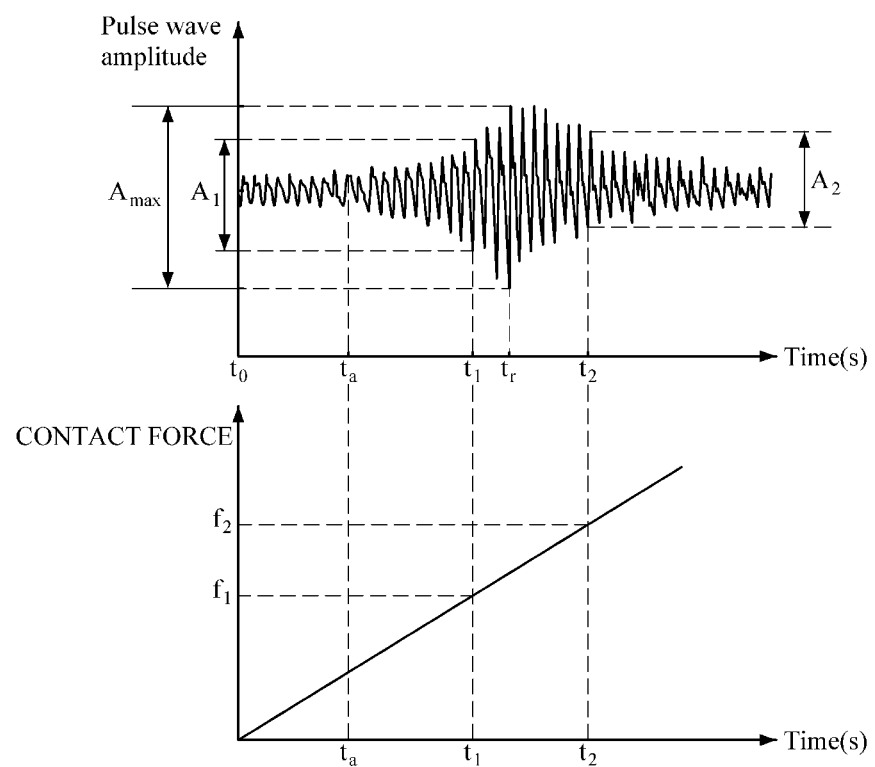
FIG. 4 illustrates graphs showing an oscillometric signal according to an embodiment.

FIG. 4 illustrates graphs showing an embodiment of an oscillometric signal. As shown in FIG. 4, the oscillometric signal may indicate a change in pulse wave signal with a change in contact force.

According to an embodiment, the processor 140 may select one or a plurality of pulse wave signals from among the pulse wave signals, which are acquired from the pulse wave sensor 110, according to preset criteria, and acquire an oscillometric signal using a combination of the selected pulse wave signals and a contact force acquired from the force sensor 120. The preset criteria may include at least one of a maximum amplitude value of each pulse wave signal, an average amplitude value, and a difference between a maximum amplitude value and a minimum amplitude value. However, the preset criteria are not limited to the above examples and a pulse wave signal measured using light of a preset wavelength may be selected from among the pulse wave signals. In an example, the processor 140 may select one pulse wave signal having the greatest difference between a maximum amplitude value and a minimum amplitude value, and acquire an oscillometric signal using the selected pulse wave signal and a contact force.

The processor 140 may estimate a blood pressure by analyzing a change in oscillometric signal with a change in contact force.

In order to measure blood pressure, the user may bring a finger into contact with the measurement surface of the pulse wave sensor 110 and gradually increase force applied to the pulse wave sensor 110. In this case, the pulse wave sensor 110 of the apparatus 100 for measuring bio-information may output a pulse wave signal in the form of an oscillometric signal as shown in an upper part of FIG. 4, and the force sensor 120 may output a contact force signal that increases with time as shown in a lower part of FIG. 4.

When the apparatus 100 for measuring bio-information which has the above-described structure is used, there may be a change in contact area between the finger and the pulse wave sensor 110 at the initial stage of gradually increasing the force since the first contact of the finger with the measurement surface of the pulse wave sensor 110. However, there is little or no change in the contact area in the time interval in which significant pulse wave information for estimating blood pressure is acquired. Therefore, when blood pressure is measured through the apparatus 100 for measuring bio-information, the contact area between the finger of the user and the pulse wave sensor 110 may be considered to be fixed. For example, in an interval from a point to in time at which the user first touches the pulse wave sensor 110 with the finger to a point $t_a$ in time at which a contact force is increased to some extent, the contact area between the finger and the pulse wave sensor 110 may increase. However, in an interval after the point $t_a$ in time, there is little change in the contact area, and a pulse wave signal for blood pressure measurement may be included in this interval.

Thus, a contact pressure between the finger and the pulse wave sensor 110 may be proportional to the contact force, and the processor 140 may estimate a blood pressure of the user using a blood pressure function having the contact force value acquired from the force sensor 120 as an input parameter. The blood pressure function may be stored in an internal or external memory of the processor 140 and a diastolic blood pressure estimation function and a systolic blood pressure estimation function may exist independently of each other. The blood pressure estimation function may be acquired in advance through experiments on a plurality of subjects.

Hereinafter, a method of acquiring the blood pressure estimation function will be described in detail.

A pulse wave signal in the form of an oscillometric signal and a contact force signal may be acquired from a plurality of subjects by using the bio-information measuring apparatus having the structure described with reference to FIGS. 1 and 2. A pulse wave signal and a contact force signal which are acquired from each of the subjects may have similar forms as shown in FIG. 4. In addition, a diastolic blood pressure and a systolic blood pressure of each subject may be measured using a separate blood pressure measurement device, such as a cuff-based blood pressure monitor. In this case, blood pressure of each subject may be measured using the bio-information measuring apparatus at a point in time at which the measured blood pressure is not significantly different from actual blood pressure of the subject at the time of measuring a pulse wave signal and a contact force signal of the subject. For example, blood pressure of the subjects may be measured while pulse wave signals and contact force signals of the subjects are being measured using the bio-information measuring apparatus. Alternatively, blood pressure of the subjects may be measured before or after pulse wave signals and the contact force signals of the subjects are measured using the bio-information measuring apparatus.

The blood pressure estimation function may be derived using the pulse wave signal, contact force signal, and blood pressure value acquired through the above procedures. For example, it is assumed that a pulse wave signal in the form of an oscillometric signal as shown in the upper part of FIG. 4 is obtained for one subject. From among pulse waves displayed in the left side of the graph on the basis of a point $t_r$ in time where an amplitude of the pulse wave signal reaches its peak value, a point $t_1$ in time where a pulse wave with an amplitude $A_1$ equal to a first percentage of the peak amplitude $A_{max}$ appears may be selected. A contact force value $f_1$ acquired through the force sensor may be obtained at the selected point $t_1$ in time. The contact force value $f_1$ and the diastolic blood pressure value measured for the corresponding subject may be mapped and stored. The above-described procedures are repeated for each of the plurality of subjects so that a plurality of contact force values and diastolic blood pressure values corresponding to each of the contact force value may be acquired.

Figure 5:
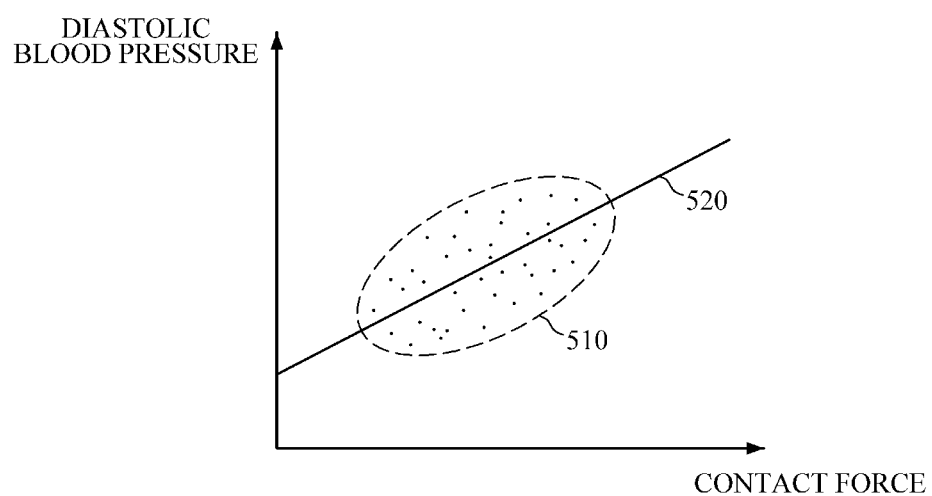
FIG. 5 is a graph in which data of contact force values and diastolic blood pressure values obtained from a plurality of subjects are plotted in XY coordinates according to an embodiment.

FIG. 5 is a graph in which data of contact force values and diastolic blood pressure values obtained from a plurality of subjects is plotted in XY coordinates. A candidate diastolic blood pressure function 520 may be obtained through a regression analysis of a data set 510. More specifically, through a regression analysis using contact force values of the data set 510 as independent variables and diastolic blood pressure values as dependent variables, a relationship between the contact force and the diastolic blood pressure may be derived and be used as a candidate diastolic blood pressure function 520. In this case, in addition to the regression analysis, other mathematical techniques may be used. A first percentage used in acquiring the data set 510 may be used as a condition for obtaining a contact force value, which is an input parameter, when the derived candidate diastolic blood pressure function 520 is used as a diastolic blood pressure estimation function.

When the first percentage is changed in FIG. 4, the contact force value $f_1$ may be changed. If the data set 510 in FIG. 5 is obtained by setting the first percentage as $X_1$, different data sets including changed contact force values and diastolic blood pressure values corresponding to the respective contact force values may be acquired by adjusting the first percentage to $X_2$, $X_3$, or the like. A candidate diastolic blood pressure function for each of the plurality of data sets may be derived, and each of the candidate diastolic blood pressure functions may output a diastolic blood pressure value that is expected when a contact force value of the data set is used as an input. An average error between the diastolic blood pressure value obtained through each of the candidate diastolic blood pressure functions and the actual diastolic blood pressure value included in the data set may be calculated and the candidate diastolic blood pressure function having the smallest average error may be selected and used as the diastolic blood pressure estimation function.

The finally determined diastolic blood pressure estimation function and the corresponding first percentage may be stored in the internal or external memory of the processor 140 of the bio-information measuring apparatus 100 described with reference to FIGS. 1 and 2 and used when the processor 140 calculates diastolic blood pressure of the user.

An example of the diastolic blood pressure estimation function acquired through the above process may be expressed by Equation 1.

$$BP_{DBP}(f_n) = af_n + b \qquad \text{Equation (1)}$$

When diastolic blood pressure is estimated using Equation 1, the user may bring a finger into contact with the bio-information measuring apparatus 100 and gradually increase the pressing force. In this case, an acquired pulse wave signal in the form of an oscillometric signal and an acquired contact force signal may have similar forms as shown in FIG. 4. If a signal as shown in FIG. 4 is obtained, a contact force value $f_1$ at a point $t_1$ in time may correspond to $f_n$ in Equation 1, wherein at the point $t_1$ in time, the pulse wave with an amplitude $A_1$ equal to a first percentage of a peak amplitude $A_{max}$ appears among the pulse waves shown in the left side of the graph with respect to a point $t_r$ in time at which the amplitude of a pulse wave signal reaches its peak value. In Equation 1, a and b are constants and may be determined according to characteristics of a sensor to be used or characteristics of subject population.

A systolic blood pressure estimation function may be acquired in a similar manner to the diastolic blood pressure estimation function described above. Referring to FIG. 4, a point $t_2$ in time at which a pulse wave with an amplitude $A_2$ equal to a second percentage of the peak amplitude $A_{max}$ appears among the pulse waves which are shown in the right side of the graph with respect to the point $t_r$ in time at which the amplitude of the pulse wave signal in the form of an oscillometric signal measured from one subject reaches its peak value. A contact force value $f_2$ acquired through the force sensor may be obtained at the selected point $t_2$ in time. The acquired contact force value f2 and the systolic blood pressure value measured from the corresponding subject may be mapped and stored. The above process is repeated on a plurality of subjects to acquire a plurality of contact force values and systolic blood pressure values corresponding to the respective contact force values.

Figure 6:
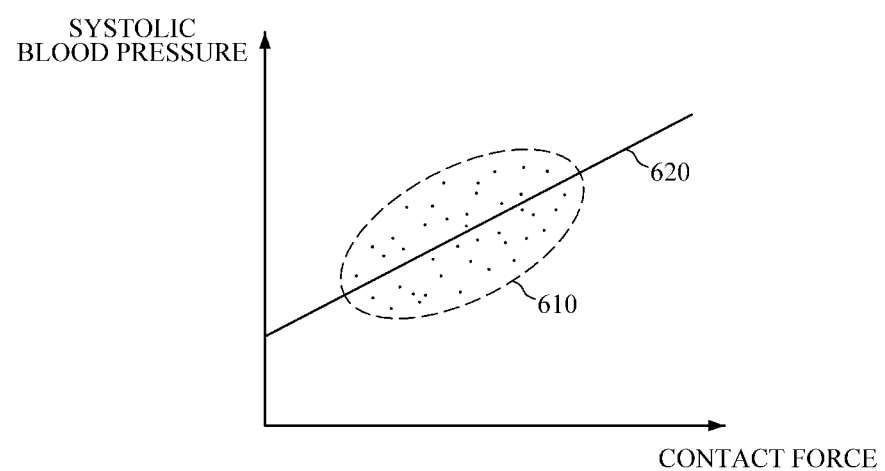
FIG. 6 is a graph in which data of contact force values and systolic blood pressure values obtained from a plurality of subjects are plotted in XY coordinates according to an embodiment.

FIG. 6 is a graph in which data of contact force values and systolic blood pressure values obtained from a plurality of subjects are plotted in XY coordinates. A systolic blood pressure candidate function 620 may be obtained through a regression analysis of a data set 610. More specifically, through a regression analysis using contact force values of the data set 610 as independent variables and systolic blood pressure values as dependent variables, a relationship between the contact force and the systolic blood pressure may be derived and be used as a candidate systolic blood pressure function 620. In this case, in addition to the regression analysis, other mathematical techniques may be used. The second percentage used for acquiring the data set 610 may be used as a condition for acquiring a contact force value, which is an input parameter, when the candidate systolic blood pressure candidate 620 is used as a candidate systolic blood pressure estimation function.

When the second percentage is changed in FIG. 4, the contact force value $f_2$ may be changed. If the data set 610 in FIG. 6 is obtained by setting the second percentage as $Y_1$, different data sets consisting of changed contact force values and systolic blood pressure values corresponding to the respective contact force values may be acquired by adjusting the second percentage to $Y_2$, $Y_3$, or the like. A candidate systolic blood pressure function for each of the plurality of data sets may be derived, and each of the candidate systolic blood pressure functions may output a systolic blood pressure value that is expected when a contact force value of the data set is used as an input. An average error between the systolic blood pressure value obtained through each of the candidate systolic blood pressure functions and the actual systolic blood pressure value included in the data set may be calculated and the candidate systolic blood pressure function having the smallest average error may be selected and used as the systolic blood pressure estimation function.

A finally determined systolic blood pressure estimation function and the corresponding second percentage may be stored in an internal or external memory of the processor 140 of the bio-information measuring apparatus 100 and be used when the processor 140 calculates the systolic blood pressure of the user.

The systolic blood pressure estimation function acquired through the above process may be expressed by Equation 2.

$$BP_{SBP}(f_m) = cf_m + d \qquad \text{Equation (2)}$$

When systolic blood pressure is estimated using Equation 2, the user may bring a finger into contact with the bio-information measuring apparatus 100 and gradually increase the pressing force. In this case, an acquired pulse wave signal in the form of an oscillometric signal and an acquired contact force signal may have similar forms as shown in FIG. 4. If a signal as shown in FIG. 4 is obtained, a contact force value $f_2$ at a point $t_2$ in time may correspond to $f_m$ in Equation 2, wherein at the point $t_2$ in time, the pulse wave with an amplitude $A_2$ equal to a second percentage of a peak amplitude $A_{max}$ appears among the pulse waves shown in the left side of the graph with respect to a point $t_r$ in time at which the amplitude of a pulse wave signal reaches its peak value. In Equation 2, a and b are constants and may be determined according to characteristics of a sensor to be used or characteristics of subject population.

In the foregoing description, the diastolic blood pressure estimation function and the systolic blood pressure estimation function are each described as a linear function, but this is merely an example. The blood pressure estimation functions may be polynomial functions or different types of function. Also, instead of the functions, a lookup table consisting of contact force values and estimated blood pressure values may be used.

<Second Measurement Mode>

In the second measurement mode, the processor 140 may operate as follows.

The processor 140 may determine whether the contact between the pulse wave sensor 110 and an object, for example, a wrist, is adequate based on a contact force measured by the force sensor 120. A pulse wave signal measured from the wrist may be affected by the degree of contact between the pulse wave sensor 110 and the wrist. When the wrist is not in sufficient contact with the pulse wave sensor 110 or is in excessively close contact with the pulse wave sensor 110, the strength of a measured pulse wave signal is reduced, which may hinder the analysis of pulse waves. Therefore, when a blood pressure is measured using a pulse waveform analysis method, the user's wrist should maintain adequately close contact with the pulse wave sensor 110. According to an embodiment, the processor 140 may determine whether the measured contact force value falls within a predetermined range. Also, the processor 140 may determine that the contact between the pulse wave sensor 110 and the wrist is adequate based on determining that the measured contact force value is within the predetermined range, and may determine that the contact between the pulse wave sensor 110 and the wrist is not adequate based on determining that the contact force value is not within the predetermined range. The processor 140 may continuously receive the contact force value from the force sensor 120 and consistently determine whether the contact between the pulse wave sensor 110 and the wrist is adequate until the end of the measurement of the pulse wave signal based on the received contact force values.

Based on determining that the contact between the pulse wave sensor 110 and the wrist is not adequate, the processor 140 may generate action guide information for inducing adequate close contact with the pulse wave sensor 110 and provide the action guide information to the user. The processor 140 may provide the action guide information to the user through an output component or interface, or may transmit the action guide information to an external device, for example, an electronic device, in which an apparatus for measuring bio-information is mounted, through a communication interface and provide the action guide information to the user through the electronic device.

The processor 140 may extract one or more features by analyzing the measured pulse wave signal and estimate a blood pressure of the user on the basis of the extracted features.

Figure 7:
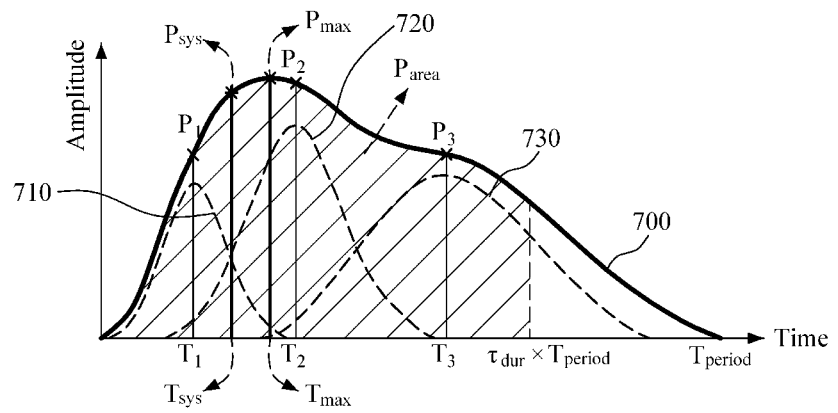
FIG. 7 is a graph for describing a feature of a pulse wave signal according to an embodiment.
Figure 8:
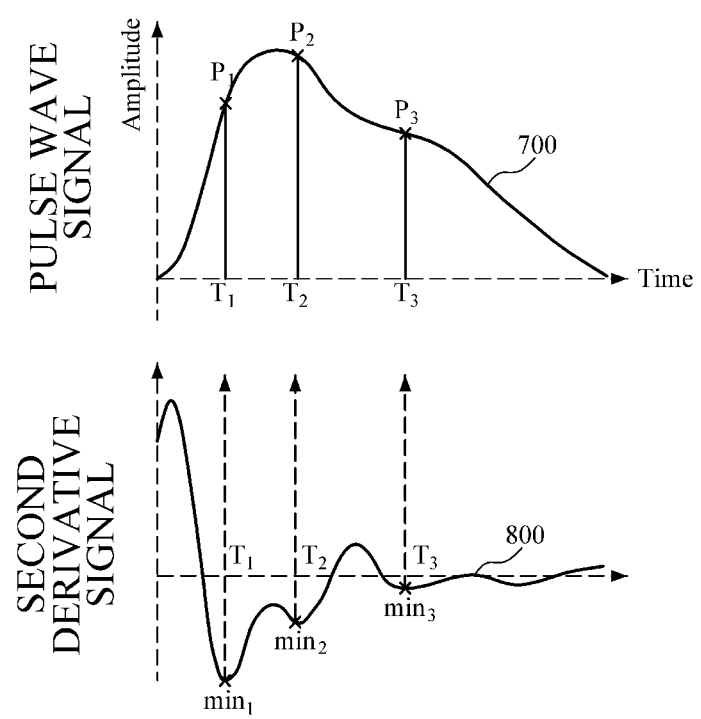
FIG. 8 is a graph for describing a method of acquiring $P_n(P_1, P_2, P_3)$ and $T_n(T_1, T_2, T_3)$ shown in FIG. 7 according to an embodiment.
Figure 9:
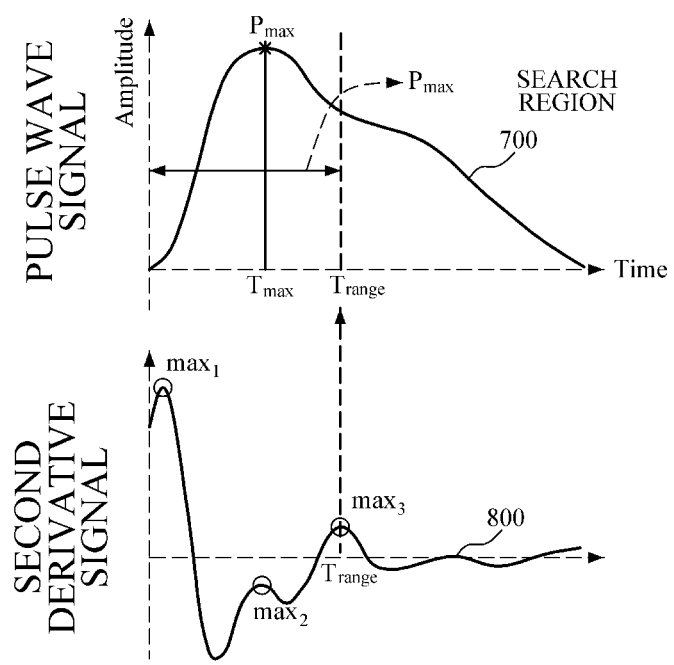
FIG. 9 is a graph for describing a method of acquiring $P_{max}$ and $T_{max}$ shown in FIG. 7 according to an embodiment.

FIG. 7 is a graph for describing a feature of a pulse wave signal, FIG. 8 is a graph for describing a method of acquiring $P_n(P_1, P_2, P_3)$ and $T_n(T_1, T_2, T_3)$ shown in FIG. 7, and FIG. 9 is a graph for describing a method of acquiring $P_{max}$ and $T_{max}$ shown in FIG. 7.

Referring to FIG. 7, a waveform of a pulse wave signal 700 may be a summation of a propagation wave 710 caused by blood propagating from the heart to peripheral parts of a body and reflection waves 720 and 730 caused by blood returning from the peripheral parts of the body.

A change in blood pressure may depend on, for example, a cardiac output, which represents the amount of blood ejected by the heart in a unit of time, and a total peripheral resistance. The change in blood pressure may be expressed by Equation 3.

$$\Delta BP = CO \times TPR \qquad \text{Equation (3)}$$

Here, ΔBP may represent a blood pressure difference between the left ventricle and the right atrium, CO may represent cardiac output, and TPR may represent total peripheral resistance.

That is, when the cardiac output increases or when the total peripheral resistance increases, blood pressure increases. Thus, the processor 140 may extract a feature highly correlated with the cardiac output and a feature highly correlated with the total peripheral resistance from a pulse wave signal, combine the two features, and estimate a blood pressure using the combined features.

According to an embodiment, the first feature is a feature related to the cardiac output, and may include, for example, $P_{max}/P_{area}$, $P_{max}/P_3$, $P_{sys}/P_3$, $P_1/P_3$, $P_2/P_3$, $1/T_{period}$, and the like. In addition, the second feature is a feature related to the total peripheral resistance, and may include $1/(T_3-T_{sys})$, $1/(T_3-T_{max})$, $1/(T_3-T_1)$, $1/(T_3-T_2)$, $P_3/P_1$, $P_2/P_1$, and the like. Here, $T_1$ may denote the time of a peak point of a first component pulse 710, $P_1$ may denote the amplitude of the pulse wave signal 700 at $T_1$, $T_2$ may denote the time of a peak point of a second component pulse 720, $P_2$ may denote the amplitude of the pulse wave signal 700 at $T_2$, $T_3$ may denote the time of a peak point of a third component pulse 730, $P_3$ may denote the amplitude of the pulse wave signal 700 at $T_3$, $T_{max}$ may denote the time of a peak point of the pulse wave signal 700 within a predetermined interval (a first interval), $P_{max}$ may denote the amplitude of the pulse wave signal 700 at $T_{max}$, $T_{sys}$ may denote the intermediate time between $T_1$ and $T_{max}$, $P_{sys}$ may denote the amplitude of the pulse wave signal 700 at $T_{sys}$, $\tau_{dur}$ may denote a setting factor ($0 \leq \tau_{dur} \leq 1$)(e.g., 0.7), and $P_{area}$ may denote the sum of amplitudes of the pulse wave signal 700 between 0 and $\tau_{dur}*T_{period}$ (a second interval). Meanwhile, $T_{sys}$ is shown as an intermediate time between $T_1$ and $T_{max}$ in FIG. 7, but embodiments are not limited thereto. For example, $T_{sys}$ may be any internally dividing point in time between $T_1$ and $T_{max}$ or any internally dividing point in time between $T_1$ and $T_2$.

Referring to FIG. 8, $P_n(P_1, P_2, P_3)$ and $T_n(T_1, T_2, T_3)$ of FIG. 7 may be obtained based on a second derivative signal 800 of the pulse wave signal 700. When the second derivative signal 800 is generated by second-order differentiating the pulse wave signal 700, may include a plurality of local minimum points $min_1$, $min_2$, and $min_3$. When the local minimum points $min_1$ to $min_3$ included in the second derivative signal 800 are arranged in a time-order sequence, the first local minimum point $min_1$ corresponds to $T_1$, the second local minimum point $min_2$ corresponds to $T_2$, and the third local minimum point $min_3$ corresponds to $T_3$. In addition, the amplitude of the PPG signal 700 at $T_1$ corresponds to $P_1$, the amplitude of the PPG signal 700 at $T_2$ corresponds to $P_2$, and the amplitude of the PPG signal 700 at $T_3$ corresponds to $P_3$.

Referring to FIG. 9, $P_{max}$ and $T_{max}$ of FIG. 7 may be obtained based on the second derivative signal 800 of the pulse wave signal 700. When the second derivative signal 800 is obtained by second-order differentiating the pulse wave signal 700, the second derivative signal 800 may include a plurality of local maximum points $max_1$, $max_2$, and $max_3$. When the local maximum points $max_1$ to $max_3$ included in the second derivative signal 800 are arranged in a time-order sequence and the time corresponding to the third maximum point $max_3$ is $T_{range}$, the $P_{max}$ search region may be determined to be a region in the range of $0 \leq time \leq T_{range}$. In this case, the time of the peak point of the pulse wave signal 700 within the $P_{max}$ search region ($0 \leq time \leq T_{range}$) corresponds to $T_{max}$ and the amplitude of the pulse wave signal 700 at $T_{max}$ corresponds to $P_{max}$.

The processor 140 may extract a first feature and a second feature from the pulse wave signal measured by the pulse wave sensor 110 using the method described above with reference to FIGS. 7 to 9. In addition, the processor 140 may estimate a blood pressure through Equations 4 and 5 using the first feature and the second feature.

$$BP_{DBP} = g(w_1 F_1 + w_2 F_2 + e)h \qquad \text{Equation (4)}$$

$$BP_{SBP} = j(w_3 F_1 + w_4 F_2 + i) + k \qquad \text{Equation (5)}$$

Here, $BP_{DBP}$ may denote diastolic blood pressure and $BP_{SBP}$ may denote systolic blood pressure. Also, $w_1$, $w_2$, $w_3$, and $w_4$ may be feature combination coefficients, e and i may each be a bias, g and j may each be a scale factor, h may denote reference diastolic blood pressure, and k may denote a reference systolic blood pressure. Here, $w_1$, $w_2$, $w_3$, $w_4$, e, g, and j may be calculated in advance through a statistically method or through a calibration process. Moreover, h and k may each be a blood pressure value estimated in the first measurement mode.

FIGS. 10 to 13 are diagrams illustrating embodiments of a pulse wave measurer. FIGS. 10 to 13 may show embodiments of the pulse wave measurer 220 of FIG. 2.

Figure 10:
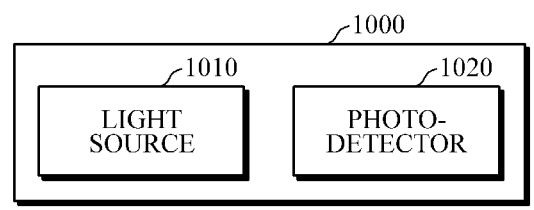
FIG. 10 is a diagram illustrating a pulse wave measurer according to an embodiment.

Referring to FIG. 10, the pulse wave measurer 1000 according to an embodiment may include a light source 1010 and a photodetector 1020.

The light source 1010 may emit light of a predetermined wavelength to a finger of a user. According to an embodiment, the light source 1010 may emit visible light, near infrared ray (NIR) light, or mid-infrared ray (MIR) light. However, the wavelength of light to be emitted from the light source 1010 may vary depending on the type of bio-information to be measured. The light source 1010 may be configured with a single light emitting structure, or may be formed as an array composed of a plurality of light emitting structures. According to an embodiment, the light source 1010 may be formed by a light emitting diode (LED), a laser diode, or a phosphor.

The photodetector 1020 may measure a pulse wave signal by detecting light reflected or scattered from the object. According to an embodiment, the photodetector 1020 may include a photodiode, a photo transistor, an image sensor (e.g., CCD or CMOS), or the like, but is not limited thereto.

Figure 11:
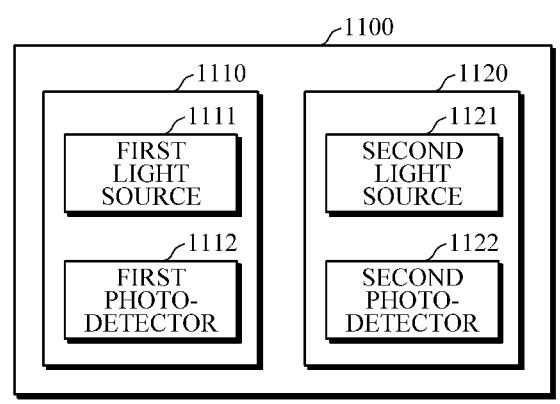
FIG. 11 is a diagram illustrating the pulse wave measurer according to an embodiment.

Referring to FIG. 11, a pulse wave measurer 1100 according to another embodiment may be formed as an array of pulse wave measurers for measuring a plurality of pulse wave signals. As shown in FIG. 11, the pulse wave measurer 1100 may include a first pulse wave measurer 1110 and a second pulse wave measurer 1120. While FIG. 11 illustrates an embodiment in which there are provided two pulse wave measurers, this is merely an example for convenience of description, and the number of pulse wave measurers constituting the pulse wave measurer array is not particularly limited.

The first pulse wave measurer 1110 may include a first light source 1111 configured to emit light of a first wavelength to an object, and a first photodetector 1112 configured to receive light of the first wavelength returning form the object irradiated by the first light source 1111 and measure a first pulse wave signal.

The second pulse wave measurer 1120 may include a second light source 1121 configured to emit light of a second wavelength to the object, and a second photodetector 1122 configured to receive light of the second wavelength returning from the object irradiated by the second light source 1121 and measure a second pulse wave signal. Here, the first wavelength and the second wavelength may be different from each other.

Figure 12:
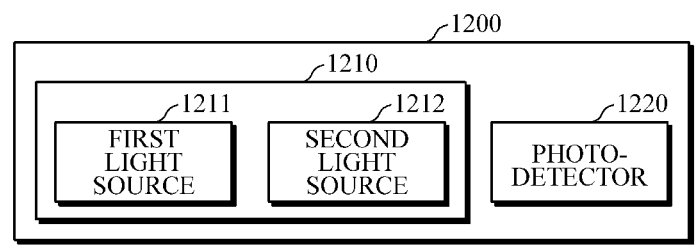
FIG. 12 is a diagram illustrating the pulse wave measurer according to an embodiment.

Referring to FIG. 12, a pulse wave measurer 1200 according to still another embodiment may include a light source portion 1210 including a plurality of light sources 1211 and 1212, and a photodetector 1220. While FIG. 12 illustrates an embodiment in which there are provided two light sources, this is merely an example for convenience of description and the number of light sources constituting the light source portion 1210 is not particularly limited.

The first light source 1211 may emit light of a first wavelength to the object, and the second light source 1212 may emit light of a second wavelength to the object. In this case, the first wavelength and the second wavelength may be different from each other.

The first light source 1211 and the second light source 1212 may be operated in a time-division manner to sequentially or simultaneously emit light to the object according to a predetermined control signal. In this case, conditions for driving light sources, such as the light emission time, driving order, current intensity, and pulse duration of the first light source 1211 and the second light source 1212, may be set in advance. The processor may drive each of the light sources 1211 and 1212 based on the light source driving conditions.

The photodetector 1220 may measure a first pulse wave signal and a second pulse wave signal by simultaneously or sequentially detecting light of the first wavelength and light of the second wavelength returning from the object which is simultaneously or sequentially irradiated by the first light source 1211 and the second light source 1212.

Figure 13:
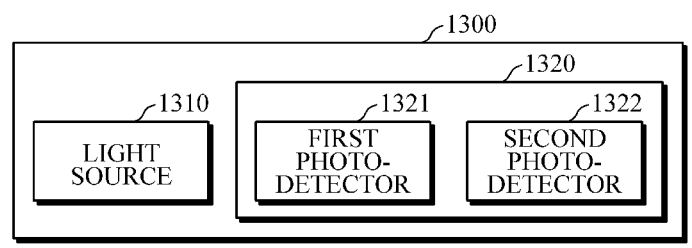
FIG. 13 is a diagram illustrating the pulse wave measurer according to an embodiment.

Referring to FIG. 13, a pulse wave measurer 1300 according to still another embodiment may include a light source 1310 and a photodetector portion 1320. The photodetector 1320 may include a first photodetector 1321 and a second photodetector 1322. While FIG. 13 illustrates an embodiment in which there are provided two photodetectors, this is merely an example for convenience of description and the number of photodetectors constituting the photodetector portion 1320 is not particularly limited.

The light source 1310 may emit light within a predetermined wavelength to the object. In this case, the light source 1310 may be configured to emit light of a wide wavelength band, including visible light.

The photodetector portion 1320 may receive light of the predetermined wavelength returning from the object to measure a plurality of pulse wave signals. To this end, the photodetector portion 1320 may be configured to have a plurality of different response characteristics.

For example, the first photodetector 1321 and the second photodetector 1322 may be formed as photodiodes having different measurement ranges so as to react to light of different wavelengths returning from the object. Alternatively, a color filter may be installed on a front surface of one of the first photodetector 1321 and the second photodetector 1322 or a different color filter may be installed on the front surface of each of the two photodetectors 1321 and 1322 such that the first photodetector 1321 and the second photodetector 1322 react to light of different wavelengths. Alternatively, the first photodetector 1321 and the second photodetector 1322 may be arranged at a different distance from the light source 1310. In this case, the photodetector arranged relatively close to the light source 1310 may detect light of a short-wavelength band, and the photodetector relatively far from the light source 1310 may detect light of a long-wavelength band.

Hereinabove, the pulse wave measurer for measuring one or more pulse wave signals is described with reference to FIGS. 10 to 13. However, the above description is merely an example, and thus embodiments are not limited thereto, such that the number and arrangement of light sources and photodetectors vary and may be changed variously depending on the utilization purpose of the pulse wave sensor and the size and shape of a touch pen in which the pulse wave sensor is installed.

Figure 14:
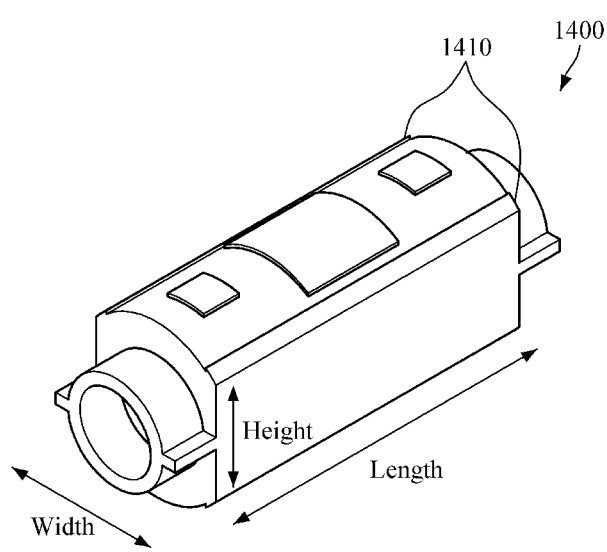
FIG. 14 is a perspective view of an apparatus for measuring bio-information according to an embodiment.

FIG. 14 is a perspective view of an apparatus for measuring bio-information according to another embodiment. An apparatus 1400 for measuring bio-information shown in FIG. 14 may be another embodiment of the apparatus 100 for measuring bio-information shown in FIG. 1.

Referring to FIG. 14, the apparatus 1400 may include an anti-slip portion 1410 for preventing a finger of a user in contact with a measurement surface of a pulse wave sensor from slipping away from the measurement surface. The anti-slip portion 1410 may be formed on an edge of a pulse wave sensor in a direction parallel to a length of the pulse wave sensor, but this is merely an example and embodiments are not limited thereto. The anti-slip portion 1410 is provided to prevent the finger of the user in contact with the measurement surface from slipping away from the measurement surface and may hence be formed of a material having a large frictional force, for example, rubber.

Figure 15A:
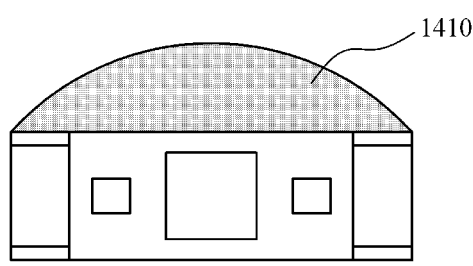
FIGS. 15A and 15B are diagrams for describing an anti-slip portion according to an embodiment.
Figure 15B:
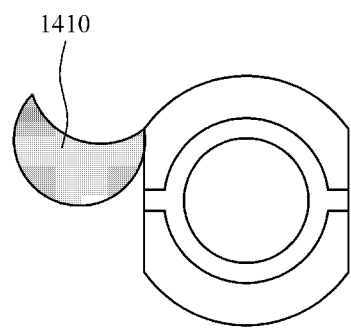

FIGS. 15A and 15B are diagrams for describing another embodiment of the anti-slip portion. More specifically, FIG. 15A is a plan view of an apparatus for measuring bio-information according to still another embodiment and FIG. 15B is a side view of the apparatus for measuring bio-information shown in FIG. 15A.

Referring to FIGS. 15A and 15B, the anti-slip portion 1410 may be formed in a shape that can be in contact with a fingertip or allows the fingertip to rest thereon, in a state where the finger is in contact with a measurement surface of a pulse wave sensor.

Figure 16:
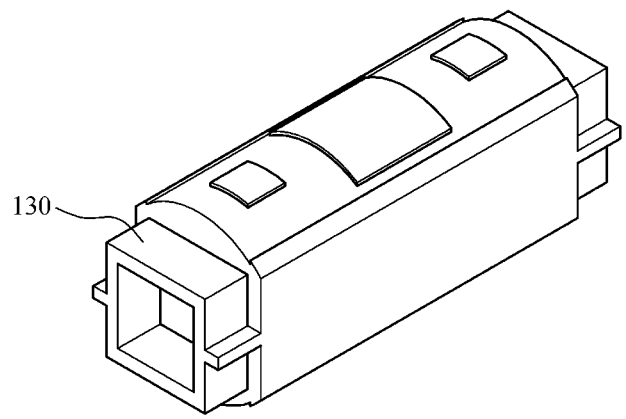
FIG. 16 is a diagram illustrating a fastener according to an embodiment.
Figure 17:
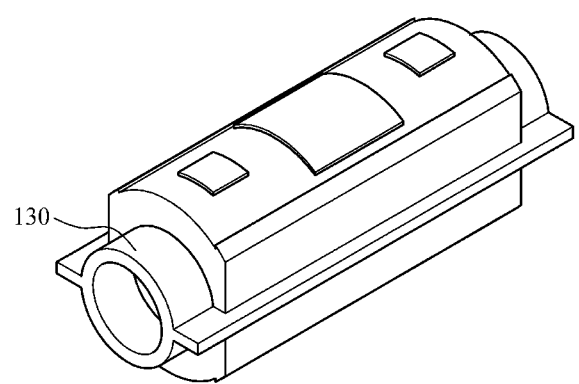
FIG. 17 is a diagram illustrating the fastener according to an embodiment.

FIGS. 16 and 17 are diagrams illustrating other embodiments of a fastener.

Referring to FIGS. 16 and 17, unlike FIG. 2, the fastener 130 may be formed in a rectangular cylindrical shape (as shown in FIG. 16), or may be formed in a shape that penetrates a pulse wave sensor and protrudes from a side surface of the pulse wave sensor, extending in a length direction (as shown in FIG. 17). However, these are merely embodiments and the shape of the fastener may vary, and may be a hexahedron, or the like.

Figure 18:
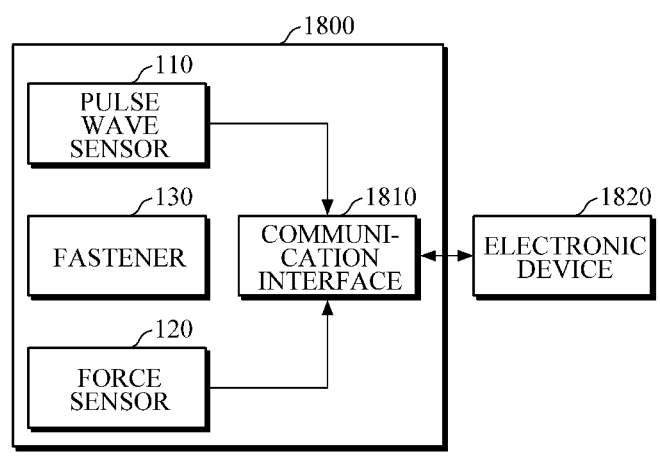
FIG. 18 is a diagram illustrating an apparatus for measuring bio-information according to an embodiment.

FIG. 18 is a diagram illustrating another embodiment of an apparatus for measuring bio-information. In the embodiment shown in FIG. 18, the functions of the processor shown in FIG. 1 are performed by an electronic device 1820.

Referring to FIG. 18, an apparatus 1800 for measuring bio-information may include a pulse wave sensor 110, a force sensor 120, a fastener 130, and a communication interface 1810. Here, the pulse wave sensor 110, the force sensor 120, and the fastener 130 are substantially the same as those described with reference to FIGS. 1 to 17, and hence detailed descriptions thereof will not be reiterated.

The communication interface 1810 may transmit a pulse wave signal measured by the pulse wave sensor 110 and a contact force measured by the force sensor 120 to the electronic device 1820. In this case, the electronic device 1820 may be an electronic device to which the apparatus 1800 for measuring bio-information is fastened.

According to an embodiment, the communication interface 1810 may communicate with the electronic device 1820 using wired or wireless communication technology. The wireless communication technology may include Bluetooth communication, Bluetooth low energy (BLE) communication, near-field communication (NFC), wireless local area network (WLAN) communication, ZigBee communication, infrared data association (IrDA) communication, wireless fidelity (Wi-Fi) direct (WFD) communication, ultra-wideband (UWB) communication, Ant+ communication, Wi-Fi communication, radio frequency identification (RFID) communication, third generation (3G) communication, fourth generation (4G) communication, fifth generation (5G) communication, and the like.

The electronic device 1820 may receive a pulse wave signal and a contact force value from the apparatus 1800 for measuring bio-information, select a measurement mode, and estimate a blood pressure by analyzing the pulse wave signal and the contact force value in the selected measurement mode.

FIGS. 19 to 22 are diagrams illustrating examples of application of the apparatus for measuring bio-information.

Figure 19:
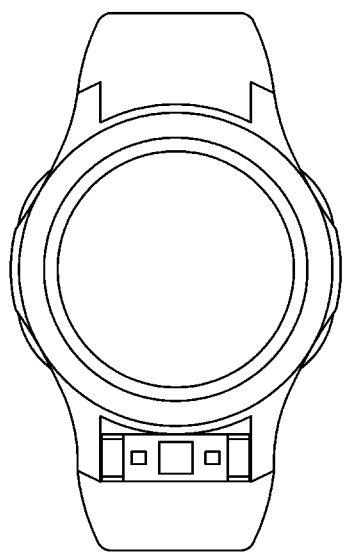
FIG. 19 is a diagram illustrating an example of application of an apparatus for measuring bio-information according to an embodiment.
Figure 20:
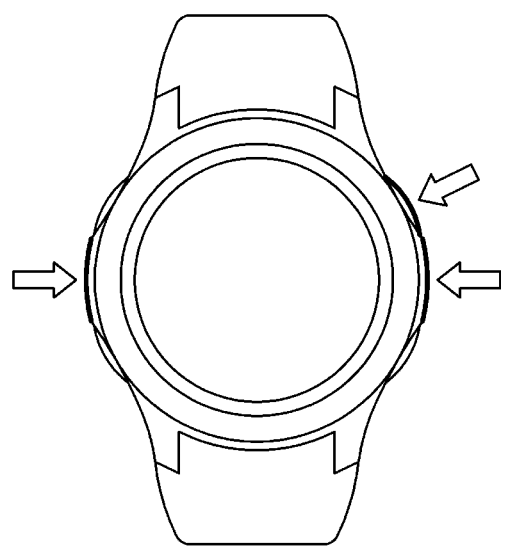
FIG. 20 is a diagram illustrating another example of application of an apparatus for measuring bio-information according to an embodiment.
Figure 21:
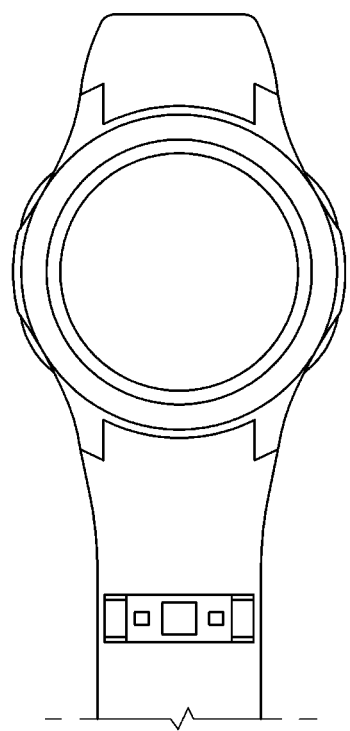
FIG. 21 is a diagram illustrating still another example of application of an apparatus for measuring bio-information according to an embodiment.
Figure 22:
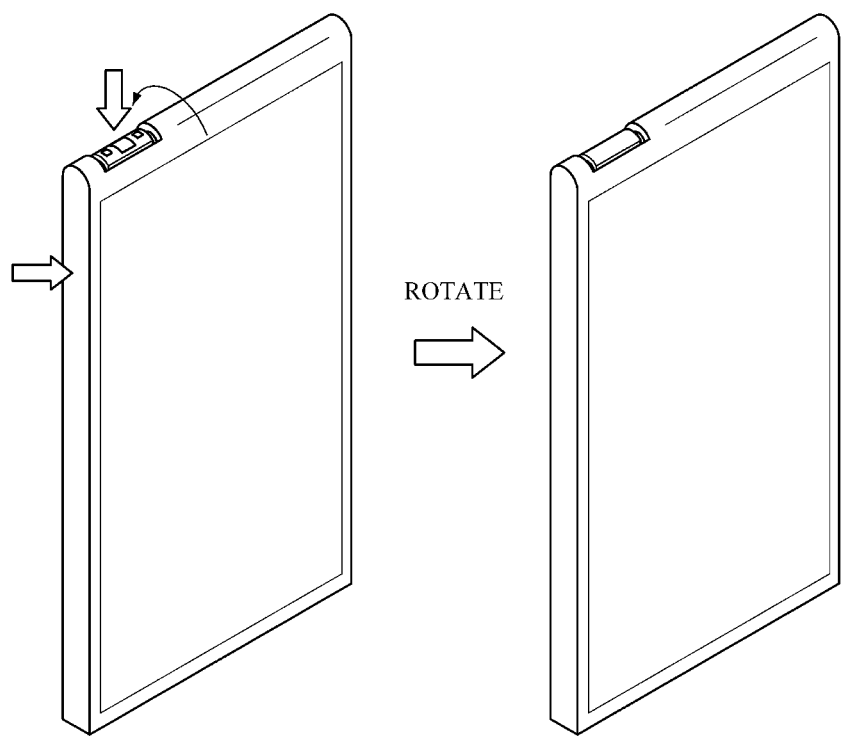
FIG. 22 is a diagram illustrating yet another example of application of an apparatus for measuring bio-information according to an embodiment.

Each of the apparatuses 100, 1400, and 1800 for measuring bio-information may be applied to a strap connector of a main body of a wrist wearable device (as shown in FIG. 19), to a button or an edge of the main body of the wrist wearable device (as shown in FIG. 20), a strap of the wrist wearable device (as shown in FIG. 21), or to an edge or side button (as shown in FIG. 22) of a smartphone.

The apparatuses 100, 1400, and 1800 illustrated in FIGS. 19 to 22 are merely embodiments and the present disclosure is not limited thereto. That is, the apparatuses 100, 1400, and 1800 may be applicable to any part without limitation as long as the part is formed as a curve or is a button on an electronic device, an accessary of the electronic device (e.g., a protective case of the electronic device or the like), a stylus pen, a joystick, or the like.

Figure 23:
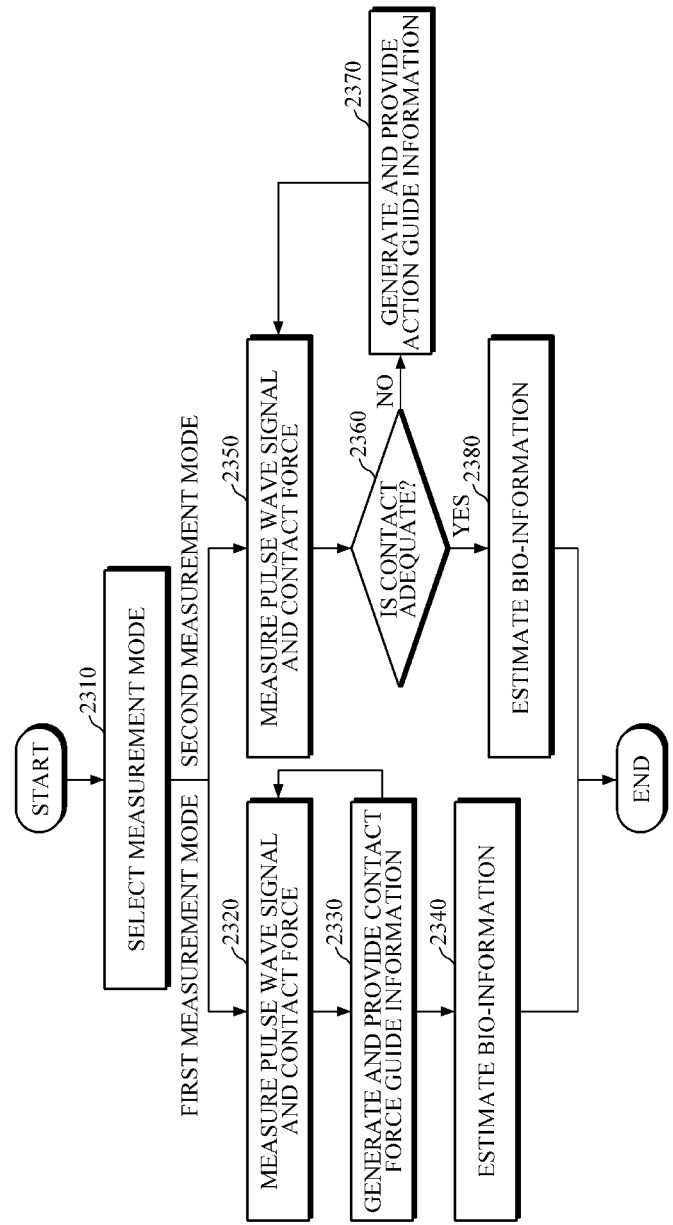
FIG. 23 is a flowchart illustrating a method of measuring bio-information according to an embodiment.

FIG. 23 is a flowchart illustrating an embodiment of a method of measuring bio-information. The method shown in FIG. 23 may be performed by the apparatuses 100 or 1400 of FIG. 1 or 14 to measure bio-information.

Referring to FIG. 23, an apparatus for measuring bio-information may select one of a first measurement mode and a second measurement mode according to a direction in which a measurement region of a pulse wave signal or a measurement surface of a pulse wave sensor is oriented (operation 2310). Here, the first measurement mode may be a blood pressure measurement mode using oscillometry based on a pulse wave signal of a finger, and the second measurement mode may be a blood pressure measurement mode using PWA based on a pulse wave signal of a wrist.

According to an embodiment, the apparatus for measuring bio-information may measure a pulse wave signal through the pulse wave sensor, and determine a measurement region of the pulse wave signal on the basis of a waveform of the measured pulse wave signal. For example, the apparatus for measuring bio-information may compare the waveform of the measured pulse wave signal to a first reference waveform and a second reference waveform. Based on determining that the waveform of the measured pulse wave signal is similar to the first reference waveform, the apparatus may determine that the measurement region of the pulse wave signal is a first region, and based on determining that the waveform of the measured pulse wave signal is similar to the second reference waveform, the apparatus may determine that the measurement region of the pulse wave signal is a second region. In this case, the first region may be a finger and the second region may be a wrist. Also, the first reference waveform may be a waveform of a pulse wave signal that is measured in advance from a finger, and the second reference waveform may be a waveform of a pulse wave signal that is measured in advance from a wrist.

According to another embodiment, the apparatus for measuring bio-information may determine a direction in which a measurement surface of the pulse wave sensor is oriented based on the position of the center of gravity of the pulse wave sensor. To this end, the pulse wave sensor may have the center of gravity biased toward one side in a height direction thereof. That is, the apparatus for measuring bio-information may determine whether the measurement surface of the pulse wave sensor is oriented in a first direction or a second direction based on a position of the center of gravity of the pulse wave sensor. Here, the first direction is a direction in which the pulse wave signal of a finger can be measured, and the second direction is a direction in which the pulse wave signal of a wrist can be measured.

According to still another embodiment, the apparatus for measuring bio-information may further include an illuminance sensor and the like. Based on an illuminance measured by the illuminance sensor, to the apparatus may determine a direction in which the measurement surface of the pulse wave sensor is oriented.

The apparatus for measuring bio-information may select one of a first measurement mode and a second measurement mode according to a direction in which the measurement region of the pulse wave signal or the measurement surface of the pulse wave sensor is oriented. According to an embodiment, the apparatus for measuring bio-information may select the first measurement mode based on the measurement region of the pulse wave signal being determined to be a first region, for example, a finger, and may select the second measurement mode based on the measurement region of the pulse wave signal being determined to be a second region, for example, a wrist. According to another embodiment, the apparatus for measuring bio-information may select the first measurement mode based on the measurement surface of the pulse wave sensor being oriented in the first direction, and may select the second measurement mode based on the measurement surface of the pulse wave sensor being oriented in the second direction.

Based on the first measurement mode being selected, the apparatus for measuring bio-information may measure one or a plurality of pulse wave signals from the finger in contact with the measurement surface, and measure a contact force between the finger and the pulse wave sensor (operation 2320). Based on the apparatus for measuring bio-information measuring a plurality of pulse wave signals, the apparatus may measure the plurality of pulse wave signals using light of different wavelengths. According to an embodiment, the apparatus for measuring bio-information may emit light to an object in contact with a contact surface formed as a curve, and receive light returning from the object to measure one or more pulse wave signals.

The apparatus for measuring bio-information may generate contact force guide information for informing of an amount of a contact force that the user should apply or reduce on the pulse wave sensor 110 while measuring the pulse wave signal, and provide the contact force guide information to the user (operation 2330). The contact force guide information may be provided before, after, or at the same time as the start of the pulse wave signal measurement. The contact force information may be continuously provided while the pulse wave sensor 110 is measuring the pulse wave signal from a finger. The contact force guide information may be provided before, after, or at the same time as the start of the pulse wave signal measurement, and may be continuously provided while the pulse wave signal is being measured. According to an embodiment, the apparatus for measuring bio-information may generate the contact force guide information based on the measured contact force value, and provide the contact force guide information to the user. For example, the apparatus for measuring bio-information may provide the contact pressure guide information based on a difference between a contact force value at a specific point in time and a contact force value to be applied by the user to the pulse wave sensor 110 at the specific point in time.

The apparatus for measuring bio-information may acquire an oscillometric signal using one or a plurality of measured pulse wave signals and the measured contact force, and estimate bio-information, for example, blood pressure, by analyzing the change in oscillometric signal with the change in contact force (operation 2340).

Based on the second measurement mode being selected, the apparatus for measuring bio-information may measure one or a plurality of pulse wave signals from a wrist in contact with the measurement surface and measure a contact force between the wrist and the pulse wave sensor (operation 2350).

The apparatus for measuring bio-information may determine whether the contact between the pulse wave sensor and the wrist is adequate based on the measured contact force (operation 2360). According to an embodiment, the apparatus for measuring bio-information may determine whether the measured contact force value is within a predetermined range. Also, the apparatus for measuring bio-information may determine that the contact between the pulse wave sensor and the wrist is adequate based on determining that the measured contact force value is within the predetermined range, and may determine that the contact between the pulse wave sensor and the wrist is not adequate based on determining that the contact force value is not within the predetermined range. The apparatus for measuring bio-information may continuously measure the contact force and consistently determine whether the contact between the pulse wave sensor and the wrist is adequate until the end of the measurement of the pulse wave signal based on the received contact force value.

Based on determining that the contact between the pulse wave sensor and the wrist is not adequate (operation 2360—NO), the apparatus for measuring bio-information may generate action guide information for inducing adequate close contact with the pulse wave sensor and provide the action guide information to the user (operation 2370).

Based on determining that the contact between the pulse wave sensor and the wrist is adequate (operation 2360—YES), the apparatus for measuring bio-information may extract one or more features by analyzing the measured pulse wave signal and estimate bio-information of the user, for example, blood pressure, based on the extracted features (operation 2380).

The current embodiments can be implemented as computer readable code in a non-transitory computer readable medium. Code and code segments constituting the computer program can be inferred by a skilled computer programmer in the art. The computer readable medium includes all types of recording media in which computer readable data are stored. Examples of the computer readable medium include a ROM, a RAM, a CD-ROM, a magnetic tape, a floppy disk, and an optical data storage. Further, the recording medium may be implemented in the form of a carrier wave such as Internet transmission. In addition, the computer readable medium may be distributed to computer systems over a network, in which computer readable code may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring bio-information, the apparatus comprising:
   a pulse wave sensor configured to measure a pulse wave signal from an object in contact with a measurement surface;
   a force sensor configured to measure a contact force between the pulse wave sensor and the object;
   an orientation sensor configured to detect a position of a center of gravity of the pulse wave sensor;
   an illuminance sensor configured to measure an illuminance; and
   a processor configured to:
      determine, based on the illuminance measured by the illuminance sensor and the position of the center of gravity of the pulse wave sensor detected by the orientation sensor, a direction in which the measurement surface of the pulse wave sensor is oriented in relation to an electronic device;
      select a measurement mode from among a plurality of measurement modes based on the direction in which the measurement surface of the pulse wave sensor is oriented morin relation to the electronic device; and
      estimate the bio-information of the object based on the measured pulse wave signal and the measured contact force in the selected measurement mode, wherein the pulse wave sensor is configured to be fastened to the electronic device such that the pulse wave sensor is rotatable around a center axis in a length direction of the pulse wave sensor,
wherein the plurality of measurement modes comprises a first measurement mode and a second measurement mode, and
wherein the first measurement mode is a first bio-information estimation mode using oscillometry based on the pulse wave signal sensed by the pulse wave sensor and a variable contact force sensed by the force sensor, and the second measurement mode is a second bio-information estimation mode using pulse waveform analysis based on the pulse wave signal sensed by the pulse wave sensor assuming a constant contact force.

2. The apparatus of claim 1, wherein the measurement surface of the pulse wave sensor is formed as a curved surface protruding toward a contact surface of the object.

3. The apparatus of claim 1, wherein the pulse wave sensor has the center of gravity biased toward one side in a first direction, and the processor is configured to determine the direction in which the measurement surface of the pulse wave sensor is oriented based on the position of the center of gravity detected by the orientation sensor.

4. The apparatus of claim 1, wherein, based on the first measurement mode being selected from among the plurality of measurement modes, the processor is further configured to acquire an oscillometric signal using the measured pulse wave signal and the measured contact force and estimate the bio-information by analyzing the acquired oscillometric signal.

5. The apparatus of claim 1, wherein, based on the first measurement mode being selected from among the plurality of measurement modes, the processor is further configured to generate contact force guide information for informing a user of an amount of contact force to be added or reduced to the pulse wave sensor based on the measured contact force.

6. The apparatus of claim 1, wherein, based on the second measurement mode being selected from among the plurality of measurement modes, the processor is further configured to determine whether a contact between the pulse wave sensor and the object is adequate based on the measured contact force and estimate the bio-information by analyzing a waveform of the measured pulse wave signal based on determining that the contact is adequate.

7. The apparatus of claim 6, wherein based on determining that the contact is not adequate, the processor is further configured to generate and provide action guide information for inducing adequate contact.

8. The apparatus of claim 6, wherein based on determining that the contact is adequate, the processor is further configured to extract one or more features from the measured pulse wave signal and estimate the bio-information using the one or more extracted features and a bio-information value estimated in the first measurement mode among the plurality of measurement modes.

9. The apparatus of claim 1, further comprising an anti-slip surface configured to prevent the object in contact with the measurement surface of the pulse wave sensor from slipping away from the measurement surface.

10. The apparatus of claim 9, wherein the anti-slip surface is formed on an edge of the pulse wave sensor in a direction parallel to the length direction of the pulse wave sensor.

11. The apparatus of claim 1, wherein the pulse wave sensor is configured to rotate around the center axis in the length direction in a state of being fastened to the electronic device, and wherein the pulse wave sensor further comprises a flange configured to stop rotation of the pulse wave sensor based on the measurement surface of the pulse wave sensor being oriented in a first direction or a second direction.

12. The apparatus of claim 1, wherein the electronic device is a wrist wearable device, and the apparatus is applied to one of a strap connector of a main body of the wrist wearable device, a button or an edge of the main body of the wrist wearable device, and a strip of the wrist wearable device.

13. A method of measuring bio-information which is performed by an apparatus for measuring bio-information which comprises a force sensor, an orientation sensor, a illuminance sensor, and a pulse wave sensor, and is fastened to an electronic device so as to be rotatable around a center axis of a length direction of the apparatus, the method comprising:
measuring a pulse wave signal from an object in contact with a measurement surface by the pulse wave sensor;
measuring a contact force between the pulse wave sensor and the object by the force sensor;
detecting a position of a center of gravity of the pulse wave sensor by the orientation sensor;
measuring an illuminance by the illuminance sensor;
determining, based on the illuminance measured by the illuminance sensor and the position of the center of gravity of the pulse wave sensor detected by the orientation sensor, a direction in which the measurement surface of the pulse wave sensor is oriented in relation to the electronic device;
selecting a measurement mode from among a plurality of measurement modes based on the direction in which the measurement surface of the pulse wave sensor is oriented in relation to the electronic device; and
estimating the bio-information based on the measured pulse wave signal and the measured contact force in the selected measurement mode,
wherein the plurality of measurement modes comprises a first measurement mode and a second measurement mode, and
wherein the first measurement mode is a first bio-information estimation mode using oscillometry based on the pulse wave signal sensed by the pulse wave sensor and a variable contact force sensed by the force sensor, and the second measurement mode is a second bio-information estimation mode using pulse waveform analysis based on the pulse wave signal sensed by the pulse wave sensor assuming a constant contact force.

14. The method of claim 13, wherein the pulse wave sensor has the center of gravity biased toward one side in a first direction,
wherein the determining of the direction in which or the measurement surface of the pulse wave sensor is oriented comprises determining the direction in which the measurement surface of the pulse wave sensor is oriented based on the position of the center of gravity, and
wherein the selecting of the measurement mode from among the plurality of measurement modes comprises selecting the first measurement mode based on determining that the measurement surface of the pulse wave sensor is oriented in the first direction, and selecting the second measurement mode based on determining that the measurement surface of the pulse wave sensor is oriented in a second direction.

15. The method of claim 13, further comprising:
based on the first measurement mode being selected from among the plurality of measurement modes, generating and providing contact force guide information for informing a user of an amount of contact force to be added or reduced to the pulse wave sensor based on the measured contact force.

16. The method of claim 13, wherein the measuring of the bio-information comprises:
based on the second measurement mode being selected from among the plurality of measurement modes, determining whether a contact between the pulse wave sensor and the object is adequate based on the measured contact force; and
estimating the bio-information based on a waveform of the measured pulse wave signal based on determining that the contact is adequate.

17. The method of claim 16, wherein the estimating of the bio-information comprises, based on determining that the contact is not adequate, generating and providing action guide information for inducing adequate contact.

18. The method of claim 16, wherein the estimating of the bio-information comprises:
based on determining that that the contact is adequate, extracting one or more features from the measured pulse wave signal; and
estimating the bio-information using the one or more extracted features and a bio-information value estimated in the first measurement mode among the plurality of measurement modes.

19. The method of claim 13, wherein the electronic device is a wrist wearable device and the apparatus is applied to one of a strap connector of a main body of the wrist wearable device, a button or an edge of the main body of the wrist wearable device, and a strip of the wrist wearable device.

* * * * *